(12) United States Patent
Hefner, Jr. et al.

(10) Patent No.: US 8,609,788 B2
(45) Date of Patent: Dec. 17, 2013

(54) POLYCYCLOPENTADIENE COMPOUNDS

(75) Inventors: Robert E. Hefner, Jr., Rosharon, TX (US); Michael J. Mullins, Houston, TX (US); Michael L. Tulchinsky, Midland, MI (US); Ernesto Occhiello, Thalwil (CH)

(73) Assignee: Dow Global Technologies LLC, Midland, MI (US)

( * ) Notice: Subject to any disclaimer, the term of this patent is extended or adjusted under 35 U.S.C. 154(b) by 0 days.

(21) Appl. No.: 13/643,321

(22) PCT Filed: Apr. 21, 2011

(86) PCT No.: PCT/US2011/000706
§ 371 (c)(1),
(2), (4) Date: Oct. 25, 2012

(87) PCT Pub. No.: WO2011/136844
PCT Pub. Date: Nov. 3, 2011

(65) Prior Publication Data
US 2013/0046065 A1    Feb. 21, 2013

(51) Int. Cl.
*C08G 8/30* (2006.01)
*C08F 283/00* (2006.01)

(52) U.S. Cl.
USPC ........................................................ 525/502

(58) Field of Classification Search
USPC ........................................................ 525/502
See application file for complete search history.

(56) References Cited

U.S. PATENT DOCUMENTS

| | | |
|---|---|---|
| 3,419,624 A | 12/1968 | Cotter et al. |
| 4,456,129 A | 6/1984 | Baber |
| 4,540,829 A | 9/1985 | Hefner, Jr. |
| 4,546,131 A | 10/1985 | Hefner, Jr. |
| 4,611,022 A | 9/1986 | Hefner, Jr. |
| 4,629,762 A | 12/1986 | Hefner, Jr. |

(Continued)

FOREIGN PATENT DOCUMENTS

| | | |
|---|---|---|
| EP | 0315089 | 5/1989 |
| GB | 1009019 | 11/1965 |

(Continued)

OTHER PUBLICATIONS

International Search Report and Written Opinion from related PCT application PCT/US2011/000706 dated Jul. 14, 2011, 12 pages.

(Continued)

*Primary Examiner* — Mike M Dollinger
(74) *Attorney, Agent, or Firm* — Brooks, Cameron & Huebsch, PLLC

(57) ABSTRACT

Embodiments of the present disclosure include polycyclopentadiene compounds represented by Formula (I): in which each X is either a hydrogen or a cyano group (N≡C—), n has an average value from zero to 20; each m independently has a value of zero to 3; p has a value of zero to 20; each R is independently a halogen, a nitrile group, a nitro group, an alkyl group, an alkoxy group, an alkenyl group, or an alkenyloxy group, where the alkyl group, the alkoxy group, the alkenyl group, and the alkenyloxy group each independently contain 1 to 6 carbon atoms; and each Q is independently hydrogen or an alkyl group containing 1 to 6 carbon atoms. Embodiments of the present disclosure also include a curable composition that includes the polycyclopentadiene compound(s) of Formula (I) and a curing amount of a resin or a catalyst amount of a catalyst and/or a cure accelerating amount of an accelerating agent.

15 Claims, 2 Drawing Sheets

(56) References Cited

U.S. PATENT DOCUMENTS

| | | | |
|---|---|---|---|
| 4,629,763 A | 12/1986 | Hefner, Jr. | |
| 4,629,764 A | 12/1986 | Hefner, Jr. | |
| 4,661,553 A | 4/1987 | Hefner, Jr. | |
| 4,707,533 A | 11/1987 | Hefner, Jr. | |
| 4,766,184 A | 8/1988 | Hefner, Jr. | |
| 4,782,124 A | 11/1988 | Hefner, Jr. et al. | |
| 5,077,380 A | 12/1991 | Hefner, Jr. et al. | |
| 5,138,101 A * | 8/1992 | Devon | 568/492 |
| 5,159,030 A | 10/1992 | Hefner, Jr. | |
| 5,206,321 A | 4/1993 | Hefner, Jr. et al. | |
| 5,281,675 A | 1/1994 | Hefner, Jr. et al. | |
| 5,428,125 A | 6/1995 | Hefner, Jr. et al. | |
| 5,442,039 A | 8/1995 | Hefner, Jr. et al. | |
| 5,602,211 A | 2/1997 | Hefner, Jr. et al. | |
| 6,307,108 B1 | 10/2001 | Argyropoulos et al. | |
| 7,321,068 B2 | 1/2008 | Papp et al. | |
| 2010/0189706 A1 | 7/2010 | Chang et al. | |
| 2011/0009559 A1* | 1/2011 | Mullins et al. | 524/589 |
| 2011/0009560 A1* | 1/2011 | Hefner et al. | 524/590 |
| 2011/0009562 A1 | 1/2011 | Mullins et al. | |
| 2011/0040046 A1 | 2/2011 | Hefner, Jr. et al. | |
| 2011/0046321 A1 | 2/2011 | Earls et al. | |
| 2011/0098380 A1* | 4/2011 | Hearn et al. | 523/400 |
| 2012/0238668 A1 | 9/2012 | Metral et al. | |
| 2012/0238709 A1 | 9/2012 | Metral et al. | |
| 2012/0289663 A1 | 11/2012 | Mullins et al. | |

FOREIGN PATENT DOCUMENTS

| | | | |
|---|---|---|---|
| WO | 8905318 | 6/1989 | |
| WO | 2009114465 | 9/2009 | |
| WO | 2009114466 | 9/2009 | |
| WO | WO 2009114383 A1 * | 9/2009 | C08G 59/32 |
| WO | WO 2009114466 A1 * | 9/2009 | C07C 39/17 |

OTHER PUBLICATIONS

International Preliminary Report on Patentability from related PCT application PCT/US2011/000706 dated Jul. 16, 2012, 7 pages.
H.E. Lee and K. Neville, "Handbook of Epoxy Resins", McGraw-Hill, New York, 1967, chapter 2, pp. 2-1 through 2-33.
Paquin, "Epoxidverbindungen und Epoxidharze", Springer-Verlag, Berlin, 1958, chapter 5, 131 pages.
Longoni, et al., "Hydroformylation and hydrocarbonylation of dicyclopentadiene with cobalt—rhodium catalytic systems promoted by triphenylphosphine: Synthesis of monoformyltricyclodecenes, diformyltricyclodecanes and di(tricyclodecenyl)ketones", Journal of Molecular Catalysis 68, 1991, 7-21.
KIRK-OTHMER, Encyclopedia of Chemical Technology, 5th edition, vol. 10, 2010, pp. 347-470.
KIRK-OTHMER, Encyclopedia of Chemical Technology, 5th edition, vol. 8, 2010, p. 219-235.
Byrne, et al. "Magnesium-Oppenauer Oxidation of Alcohols to Aldehydes and Ketones", Tetrahedron Letters, vol. 28, No. 7, 1987, pp. 769-772.
Itsuno, et al. "Reaction of Aldehyde O-Alkyl Oxime with Organometallic Compounds", Tetrahedron Letters, vol. 27, No. 26, 1986, 3033-3036.
Hirao, et al. "Versatile Synthesis of ab-acetylenic ketones by oxidative nucleophilic addition of vanadium acetylides", Tetrahedron Letters, No. 27, No. 8, 1986, pp. 933 and 934.
Adlington, et al. "Azo Anions in Synthesis t-Butylhydrazones as Acyl-anion Equivalents", Journal of the Chemical Society: Chemical Communications, 1983, 1040-1041.
Martin and Bauer "Cyanic Acid Esters From Phenols: Phenyl Cyanate", Organic Synthesis, vol. 61, 1983, pp. 35-68.
Hwang, et al. "Dielectric behavior and properties of a cyanate ester containing dicyclopentadiene 1", Journal of Appiled Polymer Science, vol. 96, No. 6, 2005, pp. 2079-2089.
Muthyala, et al. "Bridged bicyclic cores containing a 1,1-diarylethylene motif are high-affinity subtype-selective ligands for the estrogen receptor", American Chemical Society, Journal of Medicinal Chemistry (2003), 46(9), 1589-1602.
Mukherjee, et al., "Pharmacophore mapping of selective binding affinity of estrogen modulators through classical and space modeling approaches: exploration of bridged-cyclic compounds with diarylethylene linkage", Journal of Chemical Information and Modeling (2007), 47(2), 475-487.
Lekishvili, et al. "Polymers with organic-inorganic chains for the light-valve projection", Soobshcheniya Akademii Nauk Gruzinskoi SSR (1980), 98(1), 85-88.
Green, et al. "Protective Groups in Organic Synthesis", Wiley-Interscience, New York, 1999, 67-74, 708-711.
Krompiec, et al. "Isomerization of allyl aryl ethers to their 1-propenyl derivatives catalysed by ruthenium complexes" Journal of Molecular Catalysis A: Chemical vol. 219, issue 1, 2004, 29-40.
Encyclopedia of Polymer Science and Technology, "Plastics, Resins, Rubbers, Fibers", vol. 1, 1964, 750-807.

* cited by examiner

POLYCYCLOPENTADIENE COMPOUNDS

This application is a National Stage application under 35 U.S.C. 371 of PCT/US2011/000706, filed on Apr. 21, 2011 and published as WO2011/136844A1 on Nov. 3, 2011, which claims the benefit of U.S. Provisional Application Ser. No. 61/329,320 filed Apr. 29, 2010, the entire contents of which are incorporated herein by reference in its entirety.

FIELD OF DISCLOSURE

This disclosure relates to polycyclopentadiene compounds, and in particular curable compositions that include polycyclopentadiene compounds.

BACKGROUND

Phenolic resins are synthetic materials that vary greatly in molecular structure. This variety allows for a multitude of applications for these resins. One example of a phenolic resin is polycyclopentadiene diphenol, which is discussed in U.S. Pat. Nos. 3,419,624 and 4,546,129. Polycyclopentadiene diphenol may be used as a curing agent and/or to prepare the corresponding epoxy, cyanate and/or allyl thermosettable resin. These curing agents and/or resins can provide enhanced physical and/or mechanical properties to a cured composition due to the presence of the dicyclopentadienyl moiety and/or the functional group (e.g., the diphenol moiety). For example, cured compositions formed from such resins can have both a high glass transition temperature (Tg) and a relatively low water uptake.

To achieve these properties, however, would require the resin to have a high functionality (i.e., chemical groups available for cross linking). As the functionality increases in these resins, so does their molecular weight. As the molecular weight increases, so does the melt viscosity of the resin. Having a high melt viscosity can lead to difficulties in using such resins.

SUMMARY

For the various embodiments, the polycyclopentadiene compounds of the present disclosure are represented by the following Formula I:

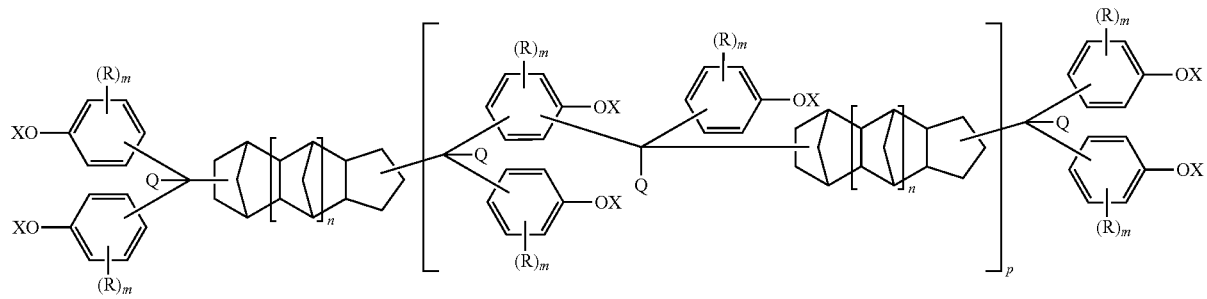

(Formula I)

in which each X is either a hydrogen or a cyano group $$(N\equiv C-),$$

each $n$ independently has a value of zero to 20; each $m$ independently has a value of zero to 3; $p$ has a value of zero to 20; each R is independently a halogen, a nitrile group, a nitro group, an alkyl group, or an alkoxy group, where the alkyl group and the alkoxy group each independently contain 1 to 6 carbon atoms; and each Q is independently hydrogen or an alkyl group containing 1 to 6 carbon atoms.

Embodiments of the present disclosure also include a curable composition that includes the polycyclopentadiene compound(s) of Formula I and a curing amount of a resin or a catalyst amount of a catalyst and/or a cure accelerating amount of an accelerating agent. For the various embodiments, when X is hydrogen the resin can be a novolac resin formed from the polycyclopentadiene compound of Formula I. The curable composition can also include a polycyclopentadiene diphenol and/or an oligomer of the polycyclopentadiene diphenol. For the various embodiments, the polycyclopentadiene compounds of Formula I can be used in fanning a cured or a partially cured composition.

The above summary of the present disclosure is not intended to describe each disclosed embodiment or every implementation of the present disclosure. The description that follows more particularly exemplifies illustrative embodiments. In several places throughout this disclosure, guidance is provided through lists of examples, which examples can be used in various combinations. In each instance, the recited list serves only as a representative group and should not be interpreted as an exclusive list.

DETAILED DESCRIPTION

Figure 1:
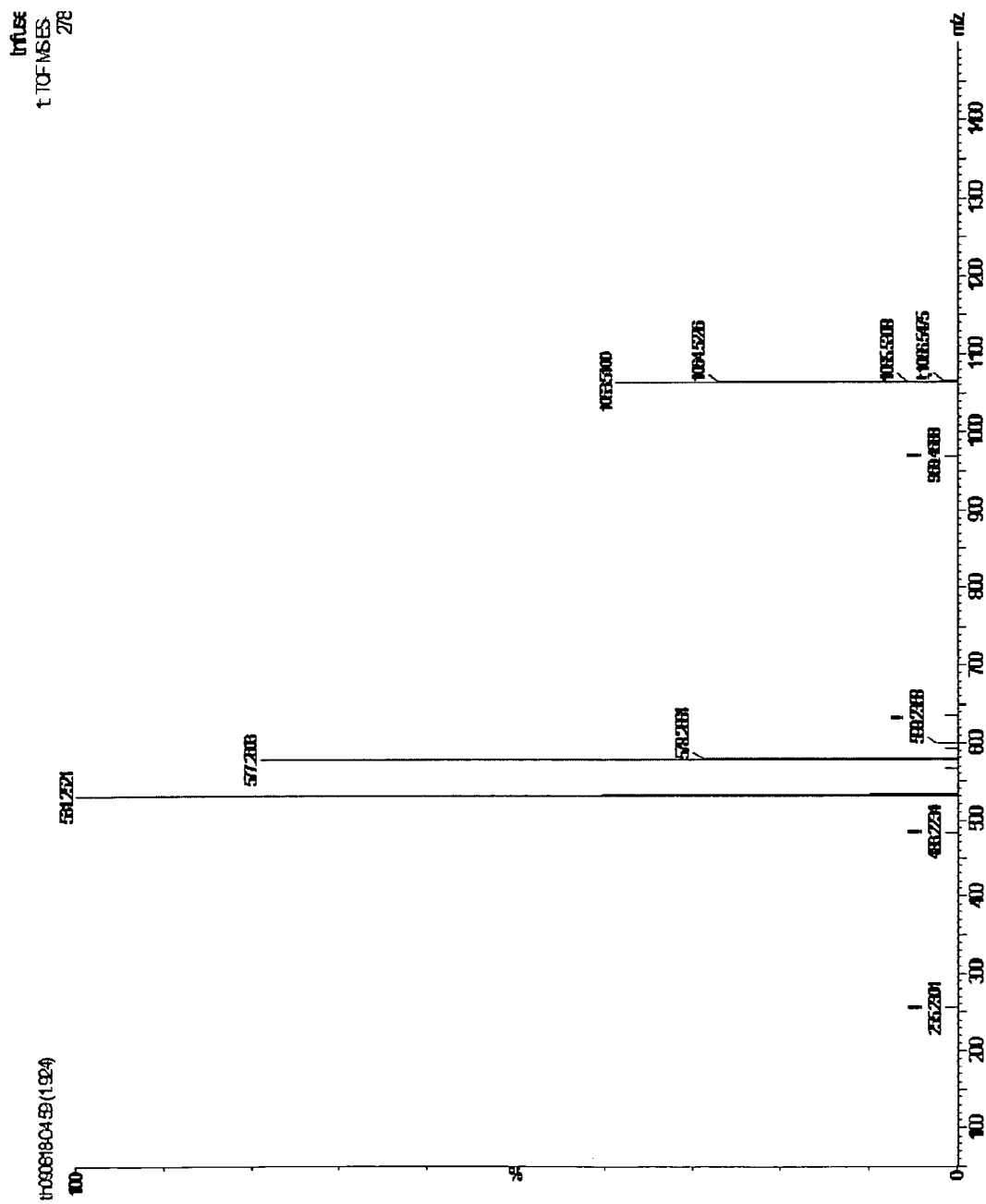
FIG. 1 provides mass spectrometric data on dicyclopentadiene polyphenol produced according to one example of the present disclosure.

The present disclosure provides for polycyclopentadiene compounds that may be useful as curing agents for epoxy resins and/or as precursors to thermoset resins. The polycyclopentadiene compounds of the present disclosure may provide high level functionality (at least four functional groups per molecule) when used in a curable composition. Surprisingly, however, the weight average molecular weights of these polycyclopentadiene compounds may be relatively low as compared to compounds having comparable functionality formed from polycyclopentadiene diphenols. As a result, melt viscosities of curable compositions that include the polycyclopentadiene compounds of the present disclosure may be lower than those utilizing compounds having comparable functionality formed from polycyclopentadiene diphenols.

For the various embodiments, the polycyclopentadiene compounds of the present disclosure may be formed from polycyclopentadiene monoaldehydes and/or dialdehydes. The use of polycyclopentadiene monoaldehydes and/or dialdehydes allows for the polycyclopentadiene compounds of the present disclosure to achieve the high level functionality with a relatively low molecular weight, which may allow for a relatively low melt viscosity of the curable composition.

Curable compositions formed with the polycyclopentadiene compounds may also provide for cured compositions that have an enhanced glass transition temperature (Tg). Additionally, it is expected that the polycyclopentadiene compounds of the present disclosure will also provide improvements in both moisture resistance and corrosion resistance, as well as enhanced electrical properties, of the cured composition, especially dissipation factor.

As used herein, "a," "an," "the," "at least one," and "one or more" are used interchangeably. The terms "includes" and "comprises" and variations thereof do not have a limiting meaning where these terms appear in the description and claims.

The term "and/or" means one, one or more, or all of the listed items.

The recitations of numerical ranges by endpoints include all numbers subsumed within that range (e.g., 1 to 5 includes 1, 1.5, 2, 2.75, 3, 3.80, 4, 5, etc.).

The term "thermoset" as used herein refers to a polymer that can solidify or "set" irreversibly when heated.

The terms "curable," "cured," "thermosettable" and "thermoset" are used synonymously throughout and mean that the composition is capable of being subjected to conditions which will render the composition to a cured or thermoset state or condition.

The term "B-stage" as used herein refers to a thermoset resin that has been thermally reacted beyond the A-stage so that the product has full to partial solubility in a solvent such as an alcohol or a ketone.

The term "alkyl group" means a saturated linear or branched monovalent hydrocarbon group including, for example, methyl, ethyl, n-propyl, isopropyl, t-butyl, pentyl, hexyl, and the like.

The term "alkoxy group" refers to groups where at least one hydrocarbon alkyl group is bonded to an oxygen. For example, a group represented by the formula —O—R or —O—R—O—R is an alkoxy group, where R is the hydrocarbon alkyl group.

For the various embodiments, the polycyclopentadiene compounds of the present disclosure are represented by the following Formula I:

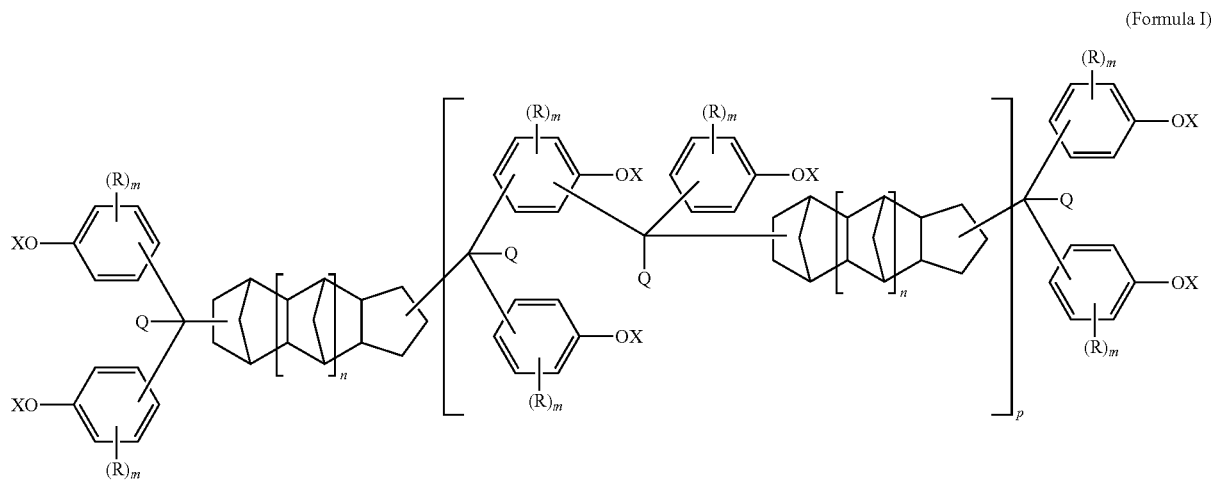

(Formula I)

in which each X is either a hydrogen or a cyano group (N≡C—), each n independently has a value from zero to 20; each m independently has a value of zero to 3; p has a value of zero to 20; each R is independently a halogen, a nitrile group, a nitro group, an alkyl group, or an alkoxy group, where the alkyl group and the alkoxy group each independently contain 1 to 6 carbon atoms; and each Q is independently hydrogen or an alkyl group containing 1 to 6 carbon atoms.

As provided herein, polycyclopentadiene compounds in which X is hydrogen may be referred to herein as a polycyclopentadiene polyphenol. Polycyclopentadiene compounds in which X is a cyano group may be referred to herein as a polycyclopentadiene polycyanate. The term polycyclopentadiene compounds, as used herein, can refer to either the polycyclopentadiene polyphenol and/or the polycyclopentadiene polycyanate, except where the context would clearly not allow for such a substitution.

For the various embodiments, the halogen of the polycyclopentadiene compounds is preferably selected from the group of fluorine, chlorine, bromine and combinations thereof. The various embodiments also provide that each n independently can have a value from zero to 8. Preferably, each n independently has a value from zero to 3, and most preferably each n independently has a value from zero to 2.

Preferably, p has a value from zero to 3, more preferably p has a value from zero to 2, and most preferably p has a value from zero to 1. For the various embodiments, the alkyl group and the alkoxy group can preferably contain 1 to 2 carbon atoms. For the various embodiments, when Q is an alkyl group it can preferably contain 1 to 2 carbon atoms. Preferably, the alkyl group and/or the alkoxy group are substituted with a halogen atom. For the various embodiments, the halogen atom in either of the alkyl group and/or the alkoxy group is each independently selected from the group consisting of chlorine, bromine and combinations thereof. For the various embodiments, the R group may also be a fused ring group, producing a naphthalene structure with the ring group that contains the —OX group such as a naphthol (1-naphthol and/or 2-naphthol), tetrahydronaphthol, indanol, and combinations thereof.

It should be understood that the composition of the compound of Formula I can be mixtures with various n and p values. For such mixtures the values of n and p can be described as number average degrees of polymerization.

For the various embodiments, when m has a value other than zero, the carbon bonded to Q

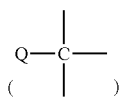

is preferably in the ortho and/or para position relative to the —OX group. It is appreciated that mixtures of compounds having the carbon bonded to the Q in both the ortho and the para position relative to the —OX group are possible. It is also possible to have the carbon bonded to Q

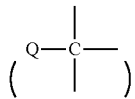

in the meta position relative to the —OX group.

For the various embodiments, m can preferably be zero to provide the polycyclopentadiene of Formula II:

Preparation of Polycyclopentadiene Polyphenols

The polycyclopentadiene polyphenols of the present disclosure can be produced from polycyclopentadiene dialdehydes and/or polycyclopentadiene diketones. For the various embodiments, polycyclopentadiene dialdehydes can be produced via hydroformylation of polycyclopentadiene, in particular, dicyclopentadiene, using syngas, a phosphine ligand, and a transition metal (from Groups 3 through 10) catalyst using a method such as described by G. Longoni, et al, J. of Molecular Catalysis 68, 7-21 (1991) or more generally in Kirk-Othmer, ENCYCLOPEDIA OF CHEMICAL TECHNOLOGY, Fifth Edition, Vol. 10, pp. 347-470 (2010). There are many variations in this process, including a method (U.S. Pat. No. 6,307,108 B1) that uses mixed polar/nonpolar solvents to ease the problem of catalyst recycle and product separation. The resulting polycyclopentadiene dialdehydes can then be condensed with phenols to form the polycyclopentadiene polyphenols of the present disclosure. Polycyclopentadiene can be prepared by heating cyclopentadiene to temperatures above 100° C. as disclosed by Kirk-Othmer, ENCYCLOPEDIA OF CHEMICAL TECHNOLOGY, Fifth Edition, Vol. 8, p. 223 (2010). All of the aforementioned references are incorporated herein in their entirety by reference.

For the various embodiments, the hydroformylation can occur at a pressure of 1 to 250 atmospheres (atm) and a temperature of 20° C. to 250° C. For the various embodiments, the syngas can contain varying amounts of carbon monoxide (CO), hydrogen ($H_2$) and, possibly, inert gases.

The reaction also can be conducted using a rhodium catalyst without a ligand as disclosed in U.S. Pat. No. 7,321,068, albeit at high syngas pressures of 200-350 atm. Examples of suitable ligands include carbon monoxide and organophosphine ligands having the general formula $PR^1 R^2 R^3$ where each $R^1$, $R^2$, and $R^3$ is a substituted or unsubstituted alkyl, an aryl, an aralkyl, an alkaryl, a halide, or a combination thereof. A specific example includes, but is not limited to, n-butyldiphenylphosphine. An example of a suitable catalyst includes, but is not limited to, $Rh(CO)_2(acetylacetonate)$.

(Formula II)

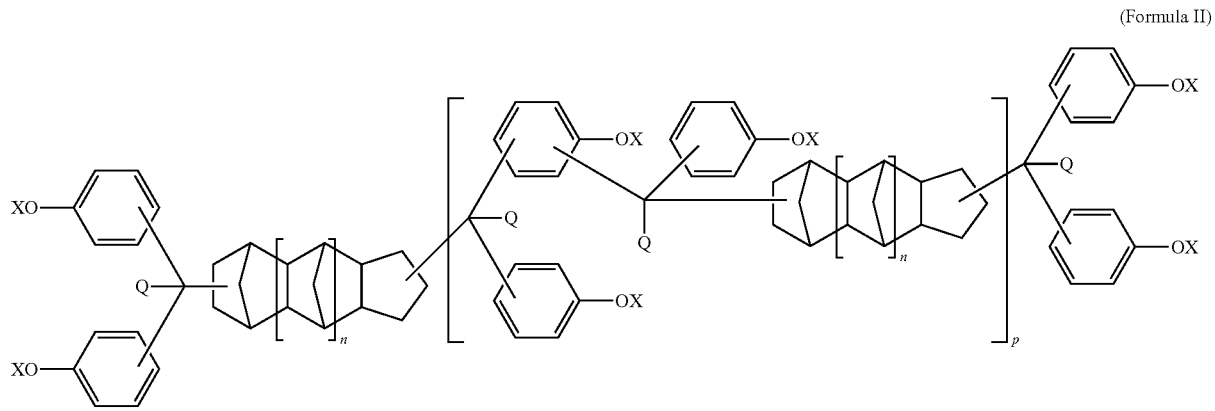

where X, n, p, and Q are as provided herein.

As appreciated, when n is zero, the polycyclopentadiene compounds of the present disclosure may also be referred to as dicyclopentadiene compounds. As used herein, however, the term polycyclopentadiene will be used, where it is understood that this term may be replaced with dicyclopentadiene when n is zero.

During the hydroformylation minor amounts, typically 5-25 weight (wt.) percent (%) or less of the total reaction products, of partially or totally saturated polycyclopentadiene monoaldehydes may also be produced along with the polycyclopentadiene dialdehydes. An example of these saturated polycyclopentadiene monoaldehydes with saturated cyclopentane ring is represented by the following Formula III, where n is as described herein:

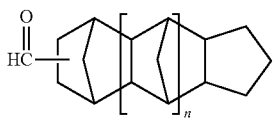

(Formula III)

The polycyclopentadiene monoaldehydes can be partially or totally separated from the polycyclopentadiene dialdehydes. For example, a distillation process could be used to separate the polycyclopentadiene monoaldehydes from the polycyclopentadiene dialdehydes.

In an additional embodiment, various weight percents of the polycyclopentadiene monoaldehydes with saturated cyclopentane ring could also be mixed with the polycyclopentadiene dialdehydes. Using mixtures of the polycyclopentadiene monoaldehydes and the polycyclopentadiene dialdehydes may allow for control of a level of functionality in the resulting curable composition. For example, whereas novolac chemistry can be used to form the polycyclopentadiene polyphenols from the polycyclopentadiene dialdehydes, novolac chemistry can also be used to form polycyclopentadiene diphenols from the polycyclopentadiene monoaldehydes. An example of the polycyclopentadiene diphenols with saturated cyclopentane ring is represented by the following Formula IV:

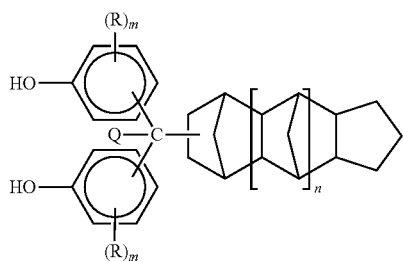

(Formula IV)

where n, m, R and Q are as described herein. Oligomers may also be present in the polycyclopentadiene diphenols. Thus, mixtures of polycyclopentadiene diphenols and polyphenols may be produced as an additional embodiment of the present disclosure.

For the various embodiments, polycyclopentadiene diketones useful in the present disclosure can be produced through a multistep synthesis, for example the chemistry given in Tetrahedron Letters, 28, 769 (1987); Tetrahedron Letters, 27, 3033 (1986); Tetrahedron Letters, 27, 933 (1986); Journal of the American Chemical Society, 107, 7179 (1985); and Journal of the Chemical Society: Chemical Communications, 1040 (1983). The polycyclopentadiene used in the present disclosure can be prepared by heating cyclopentadiene to temperatures above 100° C. as disclosed by Kirk-Othmer, ENCYCLOPEDIA OF CHEMICAL TECHNOLOGY, Fifth Edition, Vol. 8, p. 223 (2010). All of the references mentioned herein are incorporated herein in their entirety by reference.

Hydroformylation can also produce small amounts of isomeric ketones as described by Longoni. These ketones can be the predominant products when the $H_2/CO$ pressure is low (~1 atm). If these ketones are present in the product mix they can be condensed with phenol to form polyphenols of Formula V, where n, m, and R are as described herein.

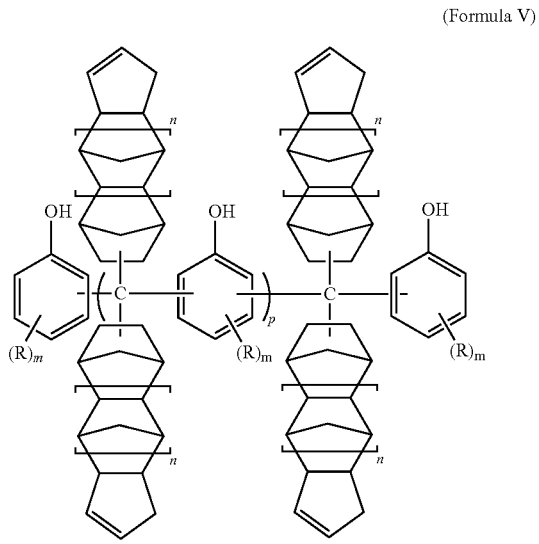

(Formula V)

As provided herein, using mixtures of the polycyclopentadiene monoaldehydes, dialdehydes, and ketones may allow control over the level of functionality in a given curable composition. So, for example, the crosslink density for a curable composition of the present disclosure can be adjusted (e.g., decreased or increased) based on the relative amounts of the polycyclopentadiene polyphenols and the polycyclopentadiene diphenols used in the composition. Adjusting the level of functionality in this way may allow for the properties such as glass transition temperature (Tg) of the cured composition to tailor to desired levels and/or balance with other properties (e.g., toughness) of the cured composition.

Moreover, it may be possible to control the amount of dicyclopentadiene and/or polycyclopentadiene moieties in the polycyclopentadiene dialdehydes of the present disclosure. The dicyclopentadiene and/or polycyclopentadiene can be formed through Diels-Alder chemistry using cyclopentadiene where, as discussed herein, the average value for n of Formula I can be from zero to 20. So, for example, when the polycyclopentadiene moieties in the polycyclopentadiene dialdehydes of the present disclosure are oligomers they can have a distribution of n values that is on average from 2 to 5. For other embodiments, n can have a value of zero or 1. The ability to control the dicyclopentadiene and/or polycyclopentadiene moieties in the polycyclopentadiene dialdehydes may also allow for the ability to control and/or tailor a crosslink density of a curable composition while retaining or even increasing potential moisture resistance properties of the cured composition.

The resulting polycyclopentadiene dialdehydes along with any of the polycyclopentadiene monoaldehydes and ketones can then undergo a novolac reaction to form the polycyclopentadiene polyphenols of the present disclosure. For the various embodiments; the novolac reaction involves the use of a phenol and an acid catalyst. For example, the polycyclopentadiene dialdehydes and molten phenol can be reacted at a temperature of 65° C. to 70° C. with stirring under a nitrogen atmosphere and in the presence of an acid catalyst. The resulting polycyclopentadiene dialdehydes, along with any of the polycyclopentadiene monoaldehydes, can then undergo a novolac reaction to form the polycyclopentadiene polyphenols of the present disclosure.

For the various embodiments, polycyclopentadiene polyphenols of the present disclosure are prepared via a condensation reaction of a mole ratio of the polycyclopentadiene dialdehydes (and any polycyclopentadiene monoaldehydes) to phenol and/or substituted phenol, such as, for example, o-cresol, m-cresol, p-cresol, 2,4-dimethylphenol, 2,6-dimethylphenol, 1-naphthol, and 2-naphthol, of 1:20 to 1:6, and preferably from 1:15 to 1:8; in the presence of an acid catalyst which is preferably from 0.1 to 2, and more preferably from 0.1 to 1 wt. % based on the amount of phenol or substituted phenol compound employed. Higher mole ratios than 1:20 of the phenol or substituted phenol may be employed, however doing so requires additional energy and thus expense to recover and recycle the excess phenol or substituted phenol.

Condensation reactions employing a large excess of the phenol and/or substituted phenol have been found to favor polycyclopentadiene polyphenols having a low polydispersity and weight average molecular weight. Likewise, as the amount of the phenol and/or substituted phenol is reduced, there can be an increase in oligomers of the polycyclopentadiene polyphenols, increasing the weight average molecular weight. Increased oligomer content favors higher hydroxyl functionality per molecule which may be highly beneficial for certain end uses, for example, increasing the Tg, but at the cost of higher viscosity. Thus, while very large excesses of phenol and/or substituted phenol may be used, the present disclosure employs the molar ratio provided above to produce products rich in polycyclopentadiene polyphenol, and low in oligomers.

For the various embodiments, condensation reaction to form the polycyclopentadiene polyphenols of the present disclosure can also optionally include the use of a solvent. For these embodiments, the solvent can be inert to the reaction and reaction products may also be employed, such as, for example, toluene or xylene. The solvent may additionally serve as an agent for the azeotropic removal of water from the condensation reaction. With certain phenolic reactants with higher melt viscosities, use of one or more solvents may be beneficial for maintaining a suitable reaction medium.

Suitable acid catalysts include the protonic acids, such as hydrochloric acid, sulfuric acid, phosphoric acid; metal oxides, such as zinc oxide, aluminum oxide, magnesium oxide; organic acids, such as p-toluenesulfonic acid, oxalic acid, 3-mercapto-1-propane sulfonic acid, and combinations thereof.

For the various embodiments, the 3-mercapto-1-propane sulfonic acid is a preferred acid catalyst or co-catalyst. Surprisingly, it has been found that 3-mercapto-1-propane sulfonic acid is so highly selective in forming the polycyclopentadiene polyphenols that there is no need for an azeotropic removal of water from the reaction products. Rather, the water remains in the reactor, without quenching the novolac reaction.

Reaction temperatures and times vary, but can be from about 5 minutes to about 48 hours and reaction temperatures of from about 20° C. to about 175° C. may be employed. Preferably reaction temperatures and times can be from 15 minutes to 36 hours and reaction temperatures of from 30° C. to about 125° C. Most preferably reaction temperatures and times can be from 30 minutes to 24 hours and reaction temperatures of from 35° C. to about 75° C.

At the end of the reaction, the acidic catalyst can be removed by neutralization, for example by washing or extraction with water. Likewise, at the end of the reaction, excess phenol can be removed from the novolac product, for example, by distillation or extraction.

For the various embodiments, the polycyclopentadiene polyphenols of the present disclosure can have a polydispersity index of less than 2. For example, the polydispersity index (the measure of distribution of molecular mass in a given polymer sample) of the polycyclopentadiene polyphenols can be from 1.3 to 1.4. These types of results indicate that both the n values and the p values of each of the polycyclopentadiene polyphenols for the present disclosure are very uniform. This result is surprising, as novolac reactions often times produce products having a much larger polydispersity (e.g., from 2 to 5). Having a uniform chain length for the polycyclopentadiene polyphenols for the present disclosure allow for more desirable viscosity predictability in the viscosity of the curable compositions of the present disclosure.

The polydispersity values for certain of the polycyclopentadiene polyphenols of the present disclosure are indicative of an increase in the level of functionality without substantial increase in Mw. High functionality and the resultant high crosslink density can provide very desirable high Tg For the various embodiments, starting with the polycyclopentadiene dialdehydes allows for a high level of functionality to be achieved in the resulting polycyclopentadiene polyphenols without a large increase in the compound's Mw. This is not the case with previous attempts to form polyphenols with high levels of functionality. For example, embodiments of the present disclosure provide for functionalities of about 4 at hydroxyl equivalent weights as low as about 133 grams per hydroxyl equivalent. Embodiments of the present disclosure may also allow for a scalable progression in the level of functionality to be achieved without significant increases in the molecular weight and viscosity of the curable composition.

Preparation of Polycyclopentadiene Polycyanates Resins

For the various embodiments, the polycyclopentadiene polyphenols and the polycyclopentadiene diphenols of the present disclosure can be used as novolac resin precursors to other high level of functionality, high glass transition temperature resins. For example, polycyclopentadiene polycyanate resins can be derived from the polycyclopentadiene polyphenols and the polycyclopentadiene diphenols of the present disclosure.

The polycyclopentadiene polycyanates can be prepared by reacting one or more of the polycyclopentadiene polyphenols with a stoichiometric quantity or a stoichiometric excess (up to 20 percent excess) of a cyanogen halide per phenolic hydroxyl group in the presence of a stoichiometric quantity or a stoichiometric excess (up to 20 percent excess) of a base compound per phenolic hydroxyl group and in the presence of a suitable solvent.

Reaction temperatures of −40° C. to 60° C. are operable, with reaction temperatures of −15° C. to 10° C. being preferred, and reaction temperatures of −10° C. to 0° C. being most preferred. Reaction times can vary substantially, for example, as a function of the reactants being employed, the reaction temperature, solvent(s) used, the scale of the reaction, and the like, but are generally between 15 minutes and 4 hours, with reaction times of 30 minutes to 90 minutes being preferred.

Suitable cyanogens halides include, but are not limited to, cyanogens chloride and cyanogens bromide. Alternately, the method of Martin and Bauer described in Organic Synthesis, vol. 61, pages 35-68 (1983) published by John Wiley and Sons can be used to generate the required cyanogens halide in situ from sodium cyanide and a halogen such as chlorine or bromine.

Suitable base compounds include both inorganic bases and tertiary amines such as sodium hydroxide, potassium hydroxide, trimethylamine, triethylamine, mixtures thereof, and the like. Triethylamine is a preferred base compound. Suitable solvents for the cyanation reaction can include water, aliphatic ketones, chlorinated hydrocarbons, aliphatic and cycloaliphatic ethers and diethers, aromatic hydrocarbons, mixtures thereof and the like. Acetone, methylethylketone, methylene chloride or chloroform are particularly suitable as the solvent.

Curable Composition(s)

Embodiments of the present disclosure also include a curable composition that includes the polycyclopentadiene compounds of the present disclosure and a curing amount of a resin. For example, polycyclopentadiene polyphenols of the present disclosure can be used as curing agents for di- and polyepoxides to obtain crosslinked polymeric compositions of the present disclosure.

Examples of di and polyepoxides can include aromatic epoxy compounds, alicyclic epoxy compounds, aliphatic epoxy compounds, and combinations thereof.

Examples of aromatic epoxy compounds include, but are not limited to, glycidyl ether compounds of polyphenols, such as hydroquinone, resorcinol, bisphenol A, bisphenol F, 4,4'-dihydroxybiphenyl, tetrabromobisphenol A, 2,2-bis(4-hydroxyphenyl)-1,1,1,3,3,3-hexafluoropropane, and 1,6-dihydroxynaphthalene. Examples of alicyclic epoxy compounds include, but are not limited to, polyglycidyl ethers of polyols having at least one alicyclic ring, or compounds including cyclohexene oxide or cyclopentene oxide obtained by epoxidizing compounds including a cyclohexene ring or cyclopentene ring with an oxidizer. Some particular examples include, but are not limited to hydrogenated bisphenol A diglycidyl ether, 3,4-epoxycyclohexylmethyl-3,4-epoxycyclohexyl carboxylate, 3,4-epoxy-1-methylcyclohexyl-3,4-epoxy-1-methylhexane carboxylate, 6-methyl-3,4-epoxycyclohexylmethyl-6-methyl-3,4-epoxycyclohexane carboxylate, 3,4-epoxy-3-methylcyclohexylmethyl-3,4-epoxy-3-methylcyclohexane carboxylate, 3,4-epoxy-5-methylcyclohexylmethyl-3,4-epoxy-5-methylcyclohexane carboxylate, bis(3,4-epoxycyclohexylmethyl)adipate, methylene-bis(3,4-epoxycyclohexane), 2,2-bis(3,4-epoxycyclohexyl)propane, dicyclopentadiene diepoxide, ethylene-bis(3,4-epoxycyclohexane carboxylate), dioctyl epoxyhexahydrophthalate, and di-2-ethylhexyl epoxyhexahydrophthalate.

Examples of aliphatic epoxy compounds include, but are not limited to, polyglycidyl ethers of aliphatic polyols or alkylene-oxide adducts thereof, polyglycidyl esters of aliphatic long-chain polybasic acids, homopolymers synthesized by vinyl polymerization of glycidyl acrylate or glycidyl methacrylate, and copolymers synthesized by vinyl polymerization glycidyl acrylate or glycidyl methacrylate and other vinyl monomers. Some particular examples include, but are not limited to glycidyl ethers of polyols, such as 1,4-butanediol diglycidyl ether, 1,6-hexanediol diglycidyl ether, a triglycidyl ether of glycerin, a triglycidyl ether of trimethylolpropane, a tetraglycidyl ether of sorbitol, a hexaglycidyl ether of dipentaerythritol, a diglycidyl ether of polyethylene glycol, and a diglycidyl ether of polypropylene glycol; polyglycidyl ethers of polyether polyols obtained by adding one type, or two or more types, of alkylene oxide to aliphatic polyols such as propylene glycol, trimethylolpropane, and glycerin; and diglycidyl esters of aliphatic long-chain dibasic acids.

Other epoxy compounds, which can be useful for one or more of the embodiments of this disclosure, can be found in A. M. Paquin, "Epoxidverbindungen and Epoxidharze", Springer-Verlag, Berlin, (1958), and/or in Lee, "Handbook of Epoxy Resins", (1967), both of which are incorporated herein by reference in their entirety. For one or more of the embodiments, a mixture of two or more different epoxy compounds can be employed.

For the various embodiments, a catalytic amount of one or more catalysts (or co-catalyst) and/or accelerators can also be used with a curable composition of the present disclosure. Examples of suitable catalysts include, but are not limited to acids, bases, salts, nitrogen and phosphorus compounds such as for example, Lewis acids such as $AlCl_3$, $BF_3$, $FeCl_3$, $TiCl_4$, $ZnCl_2$, $SnCl_4$, boric acid, protonic acids such as HCl, $H_3PO_4$, aromatic hydroxyl compounds such as phenol, p-nitrophenol, pyrocatechol, dihydroxynaphthalene, sodium hydroxide, sodium methylate, sodium phenolate, trimethylamine, triethylamine, tributylamine, diazabicyclo[2.2.2]octane, 1-methylimidazole, 2-methylimidazole, 2-phenylimidazole, quinoline, isoquinoline, tetrahydroisoquinoline, tetraethylammonium chloride, pyridine-N-oxide, tributyl phosphine, triphenyl phosphine, zinc octoate, tin octoate, zinc naphthenate, cobalt naphthenate, cobalt octoate, cobalt acetylacetonate and the like. Also suitable as catalysts are the metal chelates such as, for example, the chelates of transition metals and bidentate or tridentate ligands, particularly the chelates of iron, cobalt, zinc, copper manganese, zirconium, titanium, vanadium, aluminum and magnesium.

The quantity of catalyst and/or accelerator used, if any, depends on the structure of the particular catalyst, the structures of the polyphenol and/or the resin being cured, the cure temperature, the cure time, and the like. Generally, catalyst concentrations of from 0.01 to 2 percent by weight are preferred.

Accelerating compounds such as DMP-30 (tris(1,3,5-dimethylaminomethylene)phenol), triethanolamine, and amine salts of carboxylic acids such as triethylammonium stearate can be used.

The polycyclopentadiene polyphenols and the curing amount of the resin can be conducted at atmospheric, superatmospheric or subatmospheric pressures at temperatures of from 80° C. to 220° C., preferably from 100° C. to 220° C., more preferably from 120° C. to 200° C. The time required to complete curing depends upon the temperature employed. Higher temperatures require shorter periods of time whereas lower temperatures require longer periods of time. Generally, however, times of from 1 to 12 hours, preferably from 2 to 8 hours, more preferably from 2 to 5 hours are suitable.

The cured compositions prepared from the polycyclopentadiene polycyanates can possess the cyanate group homopolymerization structure, the polytriazine ring, unless other functionalities are present in the polycyanate that participate in the curing process. Typically, di and polycyanates have been difficult to cure, requiring high temperatures and catalysts which can interfere with many end uses such as laminates, coatings, encapsulants, adhesives and potting compounds for electronics. Additionally, the cure enthalpy of many di and polycyanates of the prior art has been sufficiently high to render controlled curing difficult. Large exothermic release of energy upon curing of many di and polycyanates of the prior art can lead to thermally damaged of parts, such as cracking, charring or delamination.

In addition, the Tg provided by the prior art polytriazine from curing of 2,6-dimethylphenol dicyclopentadiene dicyanate ester (266° C. by thermomechanical analysis, 271° C. by dynamic mechanic analysis from H-J Hwang, C-H Li, C-S Wang; Dielectric behavior and properties of a cyanate ester containing dicyclopentadiene. I.", Journal of Applied Polymer Science, volume 96, number 6, pages 2079-2089 (2005))

is lower than that provided by bisphenol A dicyanate (275.7° C. by differential scanning calorimetry analysis, see Comparative Experiment 2 herein). Thus, di or polycyanates containing the dicyclopentadienyl moiety are needed that meet or preferably exceed the Tg of bisphenol A dicyanate, while maintaining other beneficial properties imparted by the dicyclopentadienyl moiety, such as improved moisture resistance and corrosion resistance, as well as enhanced electrical properties, especially dissipation factor.

The polycyclopentadiene polycyanates of the present disclosure may help to resolve problems associated with prior art polycyanates containing the dicyclopentadienyl moiety, including reduction in Tg and unsatisfactory cure profile. The polycyclopentadiene polycyanates of the present disclosure may provide high functionality, rapid uncatalyzed cure with low enthalpy, and very high Tg (>295° C.), with improved moisture resistance, corrosion resistance, and enhanced electrical properties, which are anticipated as a result of the dicyclopentadienyl moiety.

The polycyclopentadiene polycyanates of the present disclosure have demonstrated an improvement in the uncatalyzed cure profile (cyclotrimerization to the homopolytriazine) relative to conventional dicyanates, specifically bisphenol A dicyanate. For example, the onset to cure using polycyclopentadiene polycyanates of the present disclosure was 162.6° C. versus 244.1° C. for a bisphenol A dicyanate. This favors a more rapid curing and less thermal energy required for cure onset. Cure enthalpy was also found to be 164.4 joules per gram of the polycyclopentadiene polycyanates of the present disclosure versus 588.9 joules per gram for the bisphenol A dicyanate. This lower enthalpy favors more controlled curing and the potential of reducing thermal damage caused by the curable composition. Glass transition temperature provided by the polycyclopentadiene polycyanate of the present disclosure was found to be 295.7° C., while glass transition temperature provided by the bisphenol A dicyanate was much less at 275.7° C.

For the various embodiments, curable compositions that include the polycyclopentadiene polycyanates of the present disclosure are believed to be particularly useful in electrical applications where at least the dielectric and water up-take properties of the cured composition are of importance. For example, the polycyclopentadiene polycyanates of the present disclosure provide a cured composition having a low density of polar groups (i.e., non-polar characteristics) that minimizes water attraction. This is in contrast to epoxy based curable compositions in which each polar —OH group in the cured composition can attract water. As it is believed that the cured compositions of the polycyclopentadiene polycyanates do not include polar groups, there should be an improvement in dielectric properties relative epoxy based curable compositions. It is appreciated, however, that some epoxy groups may be present in the curable compositions of the present disclosure to help provide desired properties of water up-take, adhesion and dielectric properties of the cured composition.

The polycyclopentadiene polycyanates can be cured (thermoset) by heating from 50° C. to 400° C. preferably by heating from 100° C. to 300° C., optionally in the presence of a catalytic amount of one or more catalysts (or co-catalyst) and/or accelerators, such as those provided above. Cobalt naphthenate, cobalt octoate, cobalt acetylacetonate, and manganese octoate are most preferred as the catalysts. The quantity of catalyst and/or accelerator used, if any, depends on the structure of the particular catalyst, the structure of the polycyanate being cured, the cure time, the cure temperature, and the like. Generally, catalyst concentrations of from 0.001 to 2 percent by weight are preferred.

It is also possible to partially cure (B-stage) the curable compositions of the present disclosure and then complete the curing at a later time. B-staging or prepolymerization of the curable compositions of the present disclosure can be accomplished by using lower temperatures and/or shorter curing times. Subsequent curing of the formed B-stage product can then be accomplished by increasing the temperature and/or curing time.

Embodiments of the present disclosure also include blends, partially polymerized (B-staged) product, or a cured (thermoset) product of the polycyclopentadiene polycyanate of the present disclosure with a bis or poly(maleimide); a di or polycyanate other than that of the present disclosure; a di or polycyanamide; an epoxy resin; a polymerizable mono, di, or poly(ethylenically unsaturated) monomer, including vinyl benzyl ethers, allyl and allyloxy compounds, and combinations thereof.

The polycyclopentadiene compounds of the present disclosure may also be formulated with other resins, such as, but not limited to polyurethane resins, polyester resins, epoxy resins (e.g., as provided herein), and combinations thereof. In additional embodiments, the polycyclopentadiene compounds of the present disclosure can also be employed as co-monomers with other thermosettable monomers.

Additives

The curable compositions of the present disclosure can be blended with other materials, such as solvents or diluents, fillers, pigments, dyes, flow modifiers, thickeners, reinforcing agents, mold release agents, wetting agents, stabilizers, fire retardant agents, surfactants, or combination thereof Reinforcing agents which can be employed herein include natural and synthetic fibers in the form of woven fabric, mats, monofilament, multifilament, unidirectional fibers, rovings, random fibers or filaments, inorganic fibers or whiskers, hollow spheres, among others. Suitable reinforcing materials include, for example, glass, ceramics, nylon, rayon, cotton, aramid, graphite, silicon carbide, polybenzoxazoles, polyesters such as polyalkylene terephthalates, polyethylene, polypropylene, aluminum oxide, boron, combinations thereof, or hybrids thereof Suitable fillers which can be employed herein include, for example, inorganic oxides, ceramic microspheres, plastic microspheres, or combinations thereof.

The amount of these other additives used with the curable compositions of the present disclosure can vary widely as a function of the polycyclopentadiene resin(s) of the present disclosure used, the type of curing agent(s) and/or catalyst(s) used, the processing temperature(s) employed, the type of additive(s) used, the processing method(s) used, and other known variables.

The polycyclopentadiene compounds of the present disclosure, beside other things, may be useful in preparing cured compositions for use in structural or electrical laminates and/or composites, multilayer electronic circuitry, integrated circuit packaging (such as "IC substrates"), filament windings, moldings, encapsulations, castings, composites for aerospace applications, and adhesives. Additionally, the polycyclopentadiene compounds of the present disclosure may find utility as highly functional epoxy resin curing agents useful, for example, in coatings, such as functional powder coatings and other protective coatings, where the need for a high glass transition temperature, solvent resistance, abrasion resistance and/or toughness may be beneficial. The cured compositions of the present disclosure may also be used in the form of sheets, films, fibers or other shaped articles.

The following examples are illustrative of the present invention, but are not to be construed as to limiting the scope thereof in any manner.

EXAMPLES

The following examples are given to illustrate, but not limit, the scope of this disclosure. Unless otherwise indicated, all parts and percentages are by weight. Unless otherwise specified, all instruments and chemicals used are commercially available.

Materials

Rh(CO)$_2$(acetylacetonate) (Rh(CO)$_2$acac)available from Strem Chemicals Inc. n-butyldiphenylphosphine available from Organometallics, Inc (E. Hampstead, N.H., USA).
Dicyclopentadiene available from The Dow Chemical Co.
Syngas available from Airgas Great Lakes, Inc.
Cyanogen bromide available from Sigma-Aldrich.
Triethylamine available from Sigma-Aldrich.
KBr plate available from Sigma-Aldrich.
90% purity 3-Mercaptopropane-1-sulfonic acid, sodium salt available from Sigma-Aldrich.
Hydrochloric acid available from Sigma-Aldrich.
Phenol available from Sigma-Aldrich.
Tetrahydrofuran available from Sigma-Aldrich.
Methanol available from Sigma-Aldrich.
Anhydrous acetone available from Sigma-Aldrich.
Bisphenol A dicyanate available from Huntsman International LLC as AroCy B-10 Monomeric Bisphenol A Dicyanate.

Example 1

Preparation of Dicyclopentadiene Polyphenol

A. Preparation of Dicyclopentadiene Dialdehyde

A reaction mixture of Rh(CO)$_2$acac (35.1 mg; 0.136 mmol) and n-butyldiphenylphosphine (0.33 g; 1.36 mmol) (molar ratio L/Rh=10) in dicyclopentadiene (70 g) was prepared in a purge box under dry nitrogen, and then placed in a 150 mL Parr reactor and sparged three times with 1:1 syngas (1:1 molar ratio CO:H$_2$) at 20° C. The reaction mixture was then heated to 100° C. at a pressure of 90 psi of syngas with stirring. The product formation from the reaction mixture was monitored by Gas Chromatography (GC) [Agilent 6890], where the final GC analysis of the resulting mixture showed the dicyclopentadiene dialdehyde (87 area % in GC at 10.4-10.7 minutes (min)) and the dicyclopentadiene monoaldehyde (6 area % in GC at 5.6 and 6.0 min). The dicyclopentadiene reactant was completely consumed. Very minor signals of higher molecular weight byproducts at higher retention times (21-22.5 min) were also observed. Gas chromatographic/mass spectroscopic (GC/MS) analysis [Agilent 6890 GC with Agilent 5973 Mass Selective Detector] of the reaction mixture supported the formation of the desired dicyclopentadiene dialdehyde (M$^+$=192) and saturated dicyclopentadiene monoaldehyde (M$^+$=164).

$^1$H NMR (δ, CDCl$_3$, ppm): 1.2-2.8 m (17H, CH+CH$_2$), 9.28-9.57 m (2H, CHO). $^{13}$C NMR (δ, CDCl$_3$, ppm): 23.66; 23.81; 24.35; 25.90; 25.97; 27.82; 27.97; 29.45; 29.63; 40.65; 40.92; 41.03; 41.38; 45.42; 45.50; 45.58; 45.64; 45.70; 46.07; 46.11; 48.36; 48.65; 49.17; 53.17; 53.21; 54.57; 202.86; 202.89; 202.92; 202.95; 203.03; 203.07; 203.09; 203.14

Fourier transform infrared spectrophotometric (FTIR, Nicolet Avatar 3700 DTGS FTIR (Thermo Electron Corporation)) analysis of a neat film of the dicyclopentadiene dialdehyde on a KBr plate revealed the expected strong aldehyde carbonyl stretch at 1720.4 cm$^{-1}$. The product was obtained as a brown liquid in the amount of 97.7 g.

B. Preparation of 3-Mercapto-1-propane Sulfonic Acid Catalyst

3-Mercaptopropane-1-sulfonic acid, sodium salt was added to concentrated hydrochloric acid (35.7% aqueous, 200 mL) which was magnetically stirred in a glass beaker. After covering with a sheet of Parafilm "M" (American National Can, Greenwich, Conn.) to prevent uptake of atmospheric moisture, the resulting white crystalline slurry was stirred for 5 minutes then filtered over a medium fritted glass funnel. The filtrate was rotary evaporated to give 8.88 g of a pale yellow tacky solid product which was used as the catalyst without further processing.

C. Phenolation Reaction

Dicyclopentadiene dialdehyde (48.06 g, 0.25 mole uncorrected) and molten phenol (470.5 g, 5.0 moles) were added to a 1 L glass three neck round bottom reactor. The reactor was additionally outfitted with an ambient temperature (22° C.) condenser and a thermometer, both affixed to the reactor via a Claisen adaptor, plus an overhead nitrogen inlet, a glass stirring shaft with a Teflon™ (E. I. du Pont de Nemours) stirrer blade which was coupled to a variable speed motor to provide mechanical stirring and a thermostatically controlled heating mantle.

Overhead nitrogen flow (0.5 L per minute) commenced, followed by heating, then stirring. Twenty minutes later, the temperature reached 65° C., forming a clear light yellow colored solution. At this time, addition of aliquots of the 3-mercapto-1-propane sulfonic acid (total catalyst used was 1.95 g, 0.05 mole % with respect to dicyclopentadiene dialdehyde reactant) commenced into the stirred solution. The initial aliquot of catalyst (0.39 g) induced a maximum exotherm to 70° C. after 3 minutes, turning the solution dark amber. The heating mantle was removed from the reactor, and a fan was engaged to cool the reactor exterior back to 65° C. A second aliquot of the 3-mercapto-1-propane sulfonic acid (0.22 g) was added, with continuation of the cooling. The second aliquot of the catalyst induced an exotherm to 66° C. one minute after addition, with cooling back to 65° C. after an additional 2 minutes. At this time, a third aliquot of the 3-mercapto-1-propane sulfonic acid (0.35 g) was added inducing an exotherm to 68° C. 2 minutes later. After an additional 3 minutes the temperature had cooled back to 65° C. and the cooling fan was shut off. A fourth aliquot of the 3-mercapto-1-propane sulfonic acid (0.24 g) was added with maintenance of the 65° C. reaction temperature. After 5 minutes, a fifth aliquot of the 3-mercapto-1-propane sulfonic acid (0.37 g) was added with maintenance of the 65° C. reaction temperature followed by a decline to 62.5° C. over the next 5 minutes. At this time, cooling of the reactor exterior ceased, the heating mantle was replaced on the reactor, and the final aliquot of the 3-mercapto-1-propane sulfonic acid (0.38 g) was added to the dark amber colored solution. The reaction temperature was maintained at 65° C. to 66° C. for the next 22.25 hours during which time, the course of the reaction was followed via HPLC analysis. A Hewlett Packard 1090 Liquid Chromatograph was employed using a Zorbax Eclipse® (Agilent) XDB-C8 analytical column (5 4.6×150 mm) with an Eclipse® (Agilent) XDB-C8 analytical guard column (5μ, 4.6×12.5 mm). The columns were maintained in the chromatograph oven at 40° C. Acetonitrile and water (treated with 0.05% aqueous o-phosphoric acid) were used as the eluents and were initially delivered via the pump at a rate of 1.000 mL per minute as a 70/30% solution, respectively, changing after 5 minutes to a 90/10% solution and held therein for the next 15 minutes. The acetonitrile used was HPLC grade, 100.0% purity (by gas chromatography), with a UV cutoff of 189 nm. The o-phosphoric acid used was nominally 85% pure (actual assay 85.1%). The water used was HPLC grade. A diode array detector employed for the sample analysis was set at 225 nm and the reference was set at 550 nm. After 1.6 hours of reaction, HPLC analysis revealed full conversion of the dicyclopentadiene dialdehyde to a distribution of products, with little change in the product thereafter.

At the end of the reaction time, the reactor contents were equally divided into a pair of beakers, each containing 3 L of magnetically stirred deionized (DI) water. Stirring ceased after 75 minutes and the contents of the beakers were allowed to settle overnight. The following day, each beaker was decanted to a volume of 500 mL with the decanted aqueous product disposed as waste. Both beakers were refilled with fresh DI water to 3.5 L total volume, stirring and heating commenced until 50° C. was achieved causing viscous strings of reddish amber colored product to form in the bottom of each beaker. Stirring and heating ceased and the contents of the beakers were allowed to settle overnight. The following day, each beaker was decanted to remove the aqueous product for disposal as waste. Boiling DI water (1.5 L) was added to the dark yellow orange colored product remaining in each beaker and magnetic stirring resumed with heating to a boil. Once boiling was achieved, heating ceased and stirring continued as the product slurry cooled to room temperature (20° C.). Once room temperature was reached, the solids were collected by decantation through filter paper. The solids were added to a ceramic dish and dried in the vacuum oven at 100° C. for 16 hours, removed, ground to a fine powder and dried in the vacuum oven for an additional 6.5 hours to provide 119.79 g of the dicyclopentadiene polyphenol as a mustard yellow colored powder. FTIR spectrophotometric analysis of a KBr pellet revealed complete disappearance of the aldehyde carbonyl stretch at 1720.4 $cm^{-1}$ with appearance of strong aromatic ring absorbance at 1610.9 (shoulder at 1595.7) and 1510.0 $cm^{-1}$, broad strong hydroxyl O—H stretching centered at 3382.2 $cm^{-1}$, and broad strong C—O stretching at 1226.7 (shoulder at 1170.7) $cm^{-1}$. HPLC analysis revealed the resulting dicyclopentadiene polyphenol included 12 components with 6 predominant components comprising 27.9, 4.2, 6.8, 11.0, 21.6 and 22.2 area %.

Example 2

Scale-up of Dicyclopentadiene Polyphenol Preparation

A. Phenolation Reaction

Dicyclopentadiene dialdehyde (144.19 g, 0.75 mole uncorrected, 1.50 aldehyde equivalent, 97.3 area % dialdehyde by GC analysis) from Example 1 and molten phenol (1412 g, 15.0 moles) were added to a 5 L glass three neck round bottom reactor. The reactor was additionally outfitted with an ambient temperature (22° C.) condenser and a thermometer, both affixed to the reactor via a Claisen adaptor, plus an overhead nitrogen inlet, a glass stirring shaft with a Teflon™ (E. I. du Pont de Nemours) stirrer blade which was coupled to a variable speed motor to provide mechanical stirring and a thermostatically controlled heating mantle and pair of cooling fans. Overhead nitrogen flow (1.0 L per min) commenced, followed by heating, then stirring. Once the temperature reached 64° C., the heating mantle was removed from the reactor, then dropwise addition of 3-mercapto-1-propane sulfonic acid (total catalyst used was 5.86 g, 0.05 mole % with respect to dicyclopentadiene dialdehyde reactant) commenced into the clear light yellow colored stirred solution. The 3-mercapto-1-propane sulfonic acid was prepared prior to the phenolation reaction using the method given in Example 1B above. During the initial 33 minutes of dropwise addition of the 3-mercapto-1-propane sulfonic acid, the reactor temperature was self-sustaining between 63° C. and 65° C. with intermittent cooling of the reactor exterior from the pair of fans. After a cumulative 36 minutes the temperature had dropped to 62° C., whereupon the heating mantle was used to heat the mixture to 64° C. to 65° C. After a cumulative 45 minutes, the final drop of 3-mercapto-1-propane sulfonic acid was added to the amber colored solution. The reaction temperature was maintained at 64° C. to 65° C. for the next 20.1 hours during which time, the course of the reaction was followed via HPLC analysis. After 3.4 hours of reaction, HPLC analysis revealed full conversion of the dicyclopentadiene dialdehyde to a distribution of products, with little change in the product when a second HPLC analysis was performed on a sample taken at 19.6 hours.

B. Product Isolation and Analytical Characterization

At the end of the reaction time, heating was stopped, the heating mantle was removed and cooling of the reactor contents to 30° C. was completed using the pair of fans. As stirring continued, DI water (3.5 L) was added to the reactor. Stirring ceased after 2 minutes and the contents of the reactor were allowed to settle, resolving into two distinct layers after 3.5 hours. The resultant aqueous layer was siphoned off and disposed as waste. The stirred reactor was refilled with fresh DI water (3.0 L) followed by continuation of stirring for 5 minutes, followed by settling overnight. The following day, the aqueous layer was siphoned off for disposal as waste. The reactor was refilled with fresh DI water (3.0 L) with stirring for 5 minutes, followed by settling overnight. The following day, the aqueous layer was siphoned off for disposal as waste. The reactor was refilled with fresh DI water (3.3 L) with stirring for 5 minutes, followed by settling for 2.6 hours. The aqueous layer was siphoned off for disposal as waste. The reactor was refilled with fresh DI water (3.5 L) with stirring for 5 minutes, followed by settling 4 hours. The aqueous layer was siphoned off for disposal as waste. The reactor was refilled with fresh DI water (3.5 L) with stirring for 5 minutes, followed by settling overnight. After siphoning off the aqueous layer, a white tacky semi-solid remained in the reactor. The entire reactor containing this product was placed in the vacuum oven and dried at 100° C. for 48 hours, followed by an additional 24 hours at 135° C. The resultant powder product comprised 387.55 grams, with HPLC analysis demonstrating the presence of significant residual phenol of about 8 area %.

C. Hot Water Extraction and Analytical Characterization

A portion (101.45 g) of the isolated powder product was added to a 2 L glass three neck round bottom reactor along with DI water (600 mL). The reactor was additionally outfitted with an ambient temperature (22° C.) condenser and a thermometer, both affixed to the reactor via a Claisen adaptor, a glass stirring shaft with a Teflon™ (E. I. du Pont de Nemours) stirrer blade, which was coupled to a variable speed motor to provide mechanical stirring and a thermostatically controlled heating mantle. Stirring and heating of the slurry of powder in water commenced. Once 74° C. was achieved, the powder fused to a viscous melt. Heating continued to 95° C. at which point the viscosity of the melt had decreased substantially. Stirring and heating was stopped and the aqueous layer was decanted off and disposed as waste. Second and third washes using fresh 1.5 L portions of DI water with heating to 95° C. were completed, followed by drying of the product in the vacuum oven at 150° C. to a constant weight of 93.14 g. HPLC analysis demonstrated reduction of residual phenol to 0.35 area % along with greater than 22 discernible components with all 11 components above 1 area % listed in order of progressively increasing retention time: 18.15 (3.50 min), 3.57 (3.63 min), 2.98 (3.84 min), 2.14 (3.94 min), 3.70 (4.00 min), 10.53 (4.13 min), 23.15 (4.40 min), 21.88 (4.58 min), 2.95 (4.81 min), 3.19 (5.02 min), 1.89 (5.30 min).

D. Replicate Phenolation and Processing Sequence

Using the method given above in item B of the present Example (Product Isolation and Analytical Characterization), the resultant powder product from replication of the phenolation reaction weighed 392.78 grams, with HPLC analysis demonstrating the presence of significant residual phenol, about an 11 area %. Hot water extraction of a portion (107.76 g) of the isolated powder product using the method given in item C of the present Example (Hot Water Extraction and Analytical Characterization) gave 93.67 g of dry product. HPLC analysis demonstrated reduction of residual phenol to 0.42 area % along with greater than 22 discernible components with all twelve components above 1 area % listed in order of progressively increasing retention time: 17.52 (3.50 min), 3.42 (3.63 min), 2.83 (3.84 min), 2.32 (3.94 min), 3.69 (4.00 min), 9.70 (4.13 min), 22.94 (4.40 min), 21.53 (4.58 min), 2.99 (4.80 min), 2.61 (5.02 min), 2.61 (5.13 min), 1.18 (5.51 min).

E. Mass Spectrometric Analysis

Mass spectrometric (MS) analyses were performed with the key experimental parameters used for the MS analyses given as follows:

Electrospray (ESI) negative ion mode
Direct infusion
Scan 50-1500µ, 1.5 seconds/scan
Nominal resolution of 10,000 (W mode)
Capillary 1400 Volt, Sample cone 60 Volt
Reference was Leucine Enkephalin A sample of the dicyclopentadiene polyphenol was dissolved in tetrahydrofuran to give a 0.25 wt % solution, which was further diluted to about 1:100 with methanol.

Figure 2:
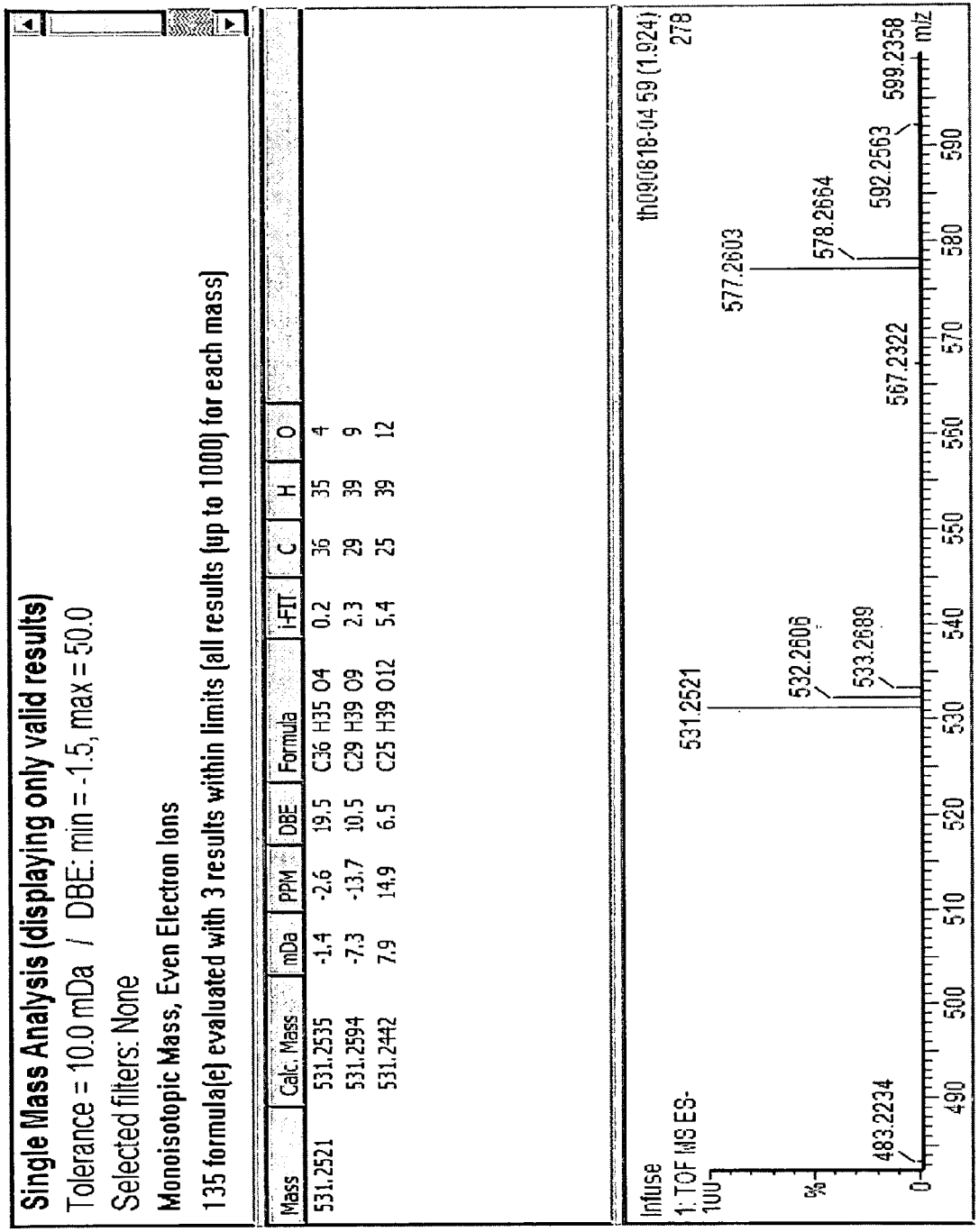
FIG. 2 provides an elemental analysis of dicyclopentadiene polyphenol produced according to one example of the present disclosure.

FIG. 1 provides mass spectrometric analysis data on the dicyclopentadiene polyphenol in the negative ion mode, which showed signals at m/z 531.2521 (equal the dicyclopentadiene tetraphenol (M–H$^-$)), and m/z 577.2603 (equal the dicyclopentadiene tetraphenol (M+formate$^-$)), and m/z 1063.5100 (equal the "in-source dimer" which is a combination of two dicyclopentadiene tetraphenols after a loss of a proton). FIG. 2 provides mass spectrometric data on the dicyclopentadiene polyphenol which confirms the elemental composition for the dicyclopentadiene tetraphenol.

Example 3

Synthesis of Dicyclopentadiene Polycyanate

A 500 milliliter, three neck, glass, round bottom reactor was charged with 26.63 grams of dicyclopentadiene polyphenol (nominally 0.20 hydroxyl equivalent) from Example 2 above and anhydrous acetone (250 milliliters, 9.39 milliliter per gram of dicyclopentadiene polyphenol). The reactor was additionally equipped with a condenser (maintained at 0° C.), a thermometer, an overhead nitrogen inlet (1 liters/minute N$_2$ gas at 22° C. used), and magnetic stirring. The solution was allowed to come to room temperature (22° C.) while being stirred. Cyanogen bromide (22.67 grams, 0.214 mole, 1.07:1 cyanogen bromide:hydroxyl equivalent ratio) was added to the solution and dissolved therein. A dry ice-acetone bath for cooling was placed under the reactor and the solution was cooled to −6° C. while being stirred. Triethylamine (20.64 grams, 0.204 mole, 1.02 triethylamine:hydroxyl equivalent ratio) was added to the reactor using a syringe in aliquots that maintained the reaction temperature at −8° C. to −3° C. The total addition time for the triethylamine was 22 minutes. After 5 minutes of triethylamine addition, the light amber colored, transparent solution transformed to a light yellow colored slurry indicative of triethylamine hydrobromide production. After 7 minutes of postreaction at −7° C. to −2° C. HPLC analysis of a sample of the reaction product revealed 24 components with each component present having a different retention time than those observed in the HPLC analysis of the dicyclopentadiene polyphenol reactant.

After a cumulative 27 minutes of postreaction at −7° C. to −2° C., the product slurry was added to a beaker of magnetically stirred deionized water (400 milliliters) and dichloromethane (250 milliliters). After 2 minutes of stirring, the mixture was added to a separatory funnel, allowed to settle, and then the dichloromethane layer recovered, with the aqueous layer discarded to waste. The dichloromethane solution was added back into the separatory funnel and extracted with fresh deionized water (400 milliliters initially, 250 milliliters thereafter) three additional times. The resultant hazy dichloromethane solution was dried over granular anhydrous sodium sulfate (25 grams) to give a clear solution that was then passed through a bed of anhydrous sodium sulfate (100 grams) supported on a 400 milliliter, medium fritted glass funnel attached to a side arm vacuum flask. The clear, light yellow colored filtrate was rotary evaporated. using a maximum oil bath temperature of 55° C. to remove the bulk of the volatiles. Additional rotary evaporation was completed at 75° C. until a vacuum of 0.4 mm Hg was achieved. The solid powder product was then placed in the vacuum oven at 75° C. and dried for 16 hours. A total of 23.14 grams of light yellow solid product was recovered. FTIR analysis of a potassium bromide pellet of the dicyclopentadiene polycyanate revealed disappearance of the hydroxyl group absorbance concurrent with the appearance of strong cyanate group absorbance at 2265.2 and 2235.4 cm$^{-1}$. HPLC analysis revealed 16 components with 3 predominant components comprising 27.9, 24.0 and 31.8 area %.

Example 4

Synthesis of the Homopolytriazine of Dicyclopentadiene Polycyanate

Differential scanning calorimetry (DSC) analysis of a portion (6.6 milligrams) of dicyclopentadiene polycyanate from Example 3 above was completed using a rate of heating of 7° C. per minute from 25° C. to 350° C. under a stream of nitrogen flowing at 35 cubic centimeters per minute. A DSC 2910 Modulated DSC (TA Instruments) was used for the analysis. No melt endotherm was detected. A single exotherm attributed to cyclotrimerization was detected with a 162.6° C. onset, a 262.3° C. midpoint, and a 304.6° C. end accompanied by an enthalpy of 164.4 joules per gram. A second scanning of the resultant homopolytriazine revealed minor exothermicity commencing at 271.1° C. A third scanning shifted the onset of minor exothermicity to 307.1° C. The homopolytriazine recovered from the DSC analysis was a transparent, amber colored, rigid solid.

Comparative Experiment 1

Synthesis of the Homopolytriazine of Bisphenol A Dicyanate

DSC analysis of bisphenol A dicyanate (10.1 milligrams) was completed using a rate of heating of 7° C. per minute from 25° C. to 350° C. under a stream of nitrogen flowing at 35 cubic centimeters per minute. A single sharp melt endotherm attributable to melting was detected with a 83.0° C. midpoint accompanied by an enthalpy of 98.7 joules per gram. A single exotherm attributed to cyclotrimerization was detected with a 244.1° C. onset, a 320.7° C. midpoint, and a 352.6° C. end accompanied by an enthalpy of 588.9 joules per gram. A second scanning of the resultant homopolytriazine revealed minor further exothermicity commencing at 319.9° C. (note: there was a gradual exothermic shift starting at 150° C.). A third scanning revealed exothermicity commencing at 209.8° C. with a more pronounced exothermic shift commencing at 320.4° C. The homopolytriazine recovered from the DSC analysis was a transparent, light amber colored, rigid solid.

Example 5

Preparation of a Clear Unfilled Casting of the Homopolytriazine of Dicyclopentadiene Polycyanate Dicyclopentadiene polycyanate (0.5 gram) from Example 3 above was added to an aluminum dish and placed into an oven preheated to 100° C. After 1 hour, the dish containing solid dicyclopentadiene polycyanate was transferred to a 150° C. oven and held therein for one hour. After 23 minutes at 150° C., the dicyclopentadiene polycyanate was a homogeneous liquid. The product was then held a 200° C. for 1 hour, at 250° C. for 1 hour and finally at 300° C. for 1 hour followed by slow cooling to room temperature (22° C.). The polytriazine product was a transparent, amber colored, rigid solid. DSC analysis of a portion (18.9 milligrams) of the product revealed a glass transition temperature of 295.7° C.

Comparative Experiment 2

Preparation of a Clear Unfilled Casting of the Homopolytriazine of Bisphenol A Dicyanate The method of Example 5 was repeated using bisphenol A dicyanate (0.5 gram). It was noted that the bisphenol A dicyanate became a homogeneous liquid while in the oven at 100° C. The polytriazine product was a transparent, yellow colored, rigid solid. DSC analysis of a portion (19.5 milligrams) of the product revealed a strong glass transition with a temperature of 275.7° C.

What is claimed:

1. A polycyclopentadiene compound of Formula I:

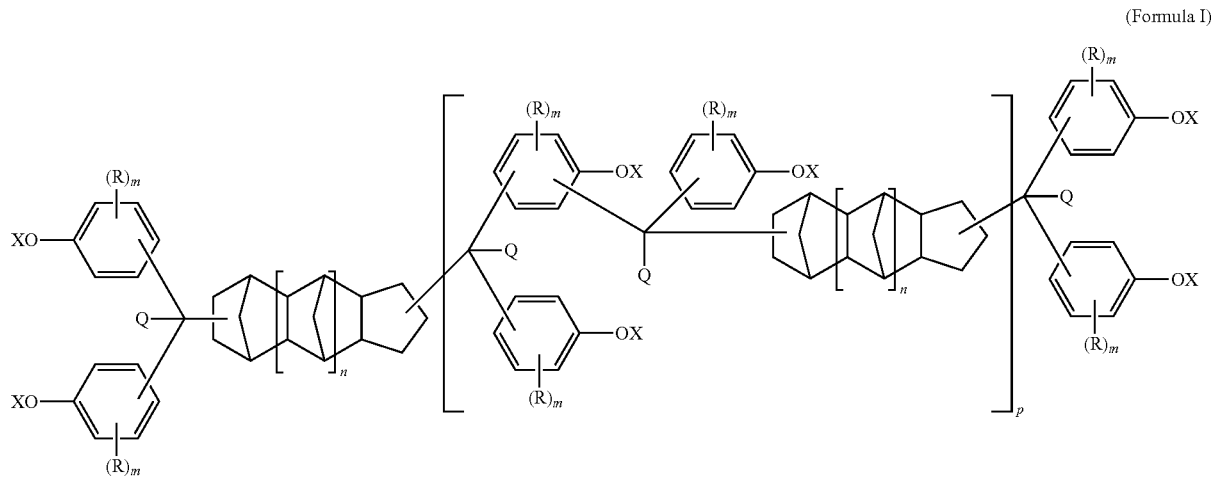

(Formula I)

in which each X is either a hydrogen or a cyano group, each n independently has a value from zero to 20; each m independently has a value of zero to 3; p has a value of zero to 20; each R is independently a halogen, a nitrile group, a nitro group, an alkyl group, or an alkoxy group, where the alkyl group and the alkoxy group each independently contain 1 to 6 carbon atoms; and each Q is independently hydrogen or an alkyl group containing 1 to 6 carbon atoms.

2. The polycyclopentadiene compound of claim 1, where the halogen is selected from the group consisting of fluorine, chlorine, bromine and combinations thereof.

3. The polycyclopentadiene compound of claim 1, where each n independently has a value from zero to 8.

4. The polycyclopentadiene compound of claim 1, where p has a value from zero to 1.

5. The polycyclopentadiene compound of claim 1, where the alkyl group and the alkoxy group contain 1 to 2 carbon atoms.

6. The polycyclopentadiene compound of claim 1, where when Q is an alkyl group contains contain 1 to 2 carbon atoms.

7. The polycyclopentadiene compound of claim 6, where the alkyl group is substituted with a halogen atom.

8. The polycyclopentadiene compound of claim 1, where the alkyl group and the alkoxy group are substituted with a halogen atom.

9. The polycyclopentadiene compound of claim 8, where the halogen atom is selected from the group consisting of chlorine, bromine and combinations thereof.

10. The polycyclopentadiene compound of claim 1, where m is zero.

11. A curable composition comprising: a polycyclopentadiene compound of Formula I as claimed in claim 1; and a curing amount of a resin or a catalyst amount of a catalyst and/or a cure accelerating amount of an accelerating agent.

12. The composition of claim 11, where X is a hydrogen and the resin is a novolac resin formed from the polycyclopentadiene compound of Formula I.

13. The composition of claim 11, including a polycyclopentadiene diphenol and/or an oligomer of the polycyclopentadiene diphenol in the curable composition.

14. The composition of claim 11, where the resin is selected from the group consisting of polyurethane resin, polyester resin, epoxy resin, and combinations thereof.

15. A cured or partially cured composition resulting from curing the polycyclopentadiene compound of Formula I as claimed in claim 1.

* * * * *